United States Patent [19]
Gruffaz et al.

[11] 3,945,999
[45] Mar. 23, 1976

[54] PROCESS FOR PREPARING SOLID BIS-(4-FURFURYLIDENAMINO-PHENYL)-METHANE

[75] Inventors: Max Gruffaz, La Multiere; Bernard Rollet, Lyon, both of France

[73] Assignee: Rhone-Poulenc, S.A., Paris, France

[22] Filed: Apr. 24, 1974

[21] Appl. No.: 463,592

[30] Foreign Application Priority Data
Apr. 26, 1973   France .............................. 73.15177

[52] U.S. Cl. ............. 260/240 G; 260/72.5; 96/56.4
[51] Int. Cl.$^2$ ................ C07D 407/10; C07D 307/28
[58] Field of Search............ 260/240 G, 347.7, 72.5

[56] References Cited
UNITED STATES PATENTS

| | | | |
|---|---|---|---|
| 2,327,773 | 8/1943 | Dickey et al..................... | 260/347.7 |
| 2,388,903 | 11/1945 | Cantrell et al.................. | 260/240 G |
| 2,500,111 | 3/1950 | Anish et al...................... | 260/240 G |
| 2,572,371 | 10/1951 | Mooney.......................... | 260/347.7 |
| 2,892,811 | 6/1959 | Irang.............................. | 260/72.5 X |

FOREIGN PATENTS OR APPLICATIONS 1,093,724   12/1967   United Kingdom

*Primary Examiner*—Allen B. Curtis
*Attorney, Agent, or Firm*—Stevens, Davis, Miller & Mosher

[57] ABSTRACT

Bis-(4-furfurylidenamino-phenyl)-methane, m.p. 90°–91°C., is made by reacting furfural with bis-(4-aminophenyl)-methane in diethyl ether. It is useful in photography.

3 Claims, No Drawings

PROCESS FOR PREPARING SOLID BIS-(4-FURFURYLIDENAMINO-PHENYL)-METHANE

The present invention provides a new imine derived from 2-furaldehyde (furfural).

The reaction of furfural with amines has been known for a long time. Thus GRIGNARD (Treatise on Organic Chemistry — volume XVIII) mentions the reactions of furfural with aniline, o-toluidine, p-toluidine, β-naphthylamine, benzidine, p-phenetidine, 4-aminodiphenylamine and 4-amino-phenol. Furfurylidenimines can be used in photographic mixtures, as described in Belgian Pat. No. 660,874. According to this patent, furfurylidenimines can be prepared in an organic solvent, at a temperature of the order of 80° to 120°C, the reaction being carried out in the presence of an acid catalyst. In the particular case wherein the amine used is bis-(4-amino-phenyl)-methane, the product obtained is a red oil. U.S. Pat. No. 2,892,811 also mentions that furfural reacts with diamino-diphenyl-methane to give a red liquid which changes into a black solid.

The present invention provides, as a new industrial product, bis-(4-furfurylidenaminophenyl)methane in the form of a crystalline solid, which is yellow in colour and has a melting point of 90°–91°C under 760 mm of mercury.

This product, which has the formula:

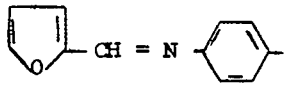

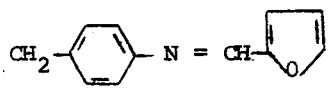

can be prepared by contacting furfural and bis-(4-aminophenyl)-methane, in a diethyl ether medium, at a temperature below the boiling point of the ether and usually not below 0°C. The reaction is generally carried out at ambient temperature (20° to 25°C) and under atmospheric pressure, with stirring of the mixture.

The reagents are usually employed in stoichiometric amounts, that is to say two mols of furfural are used per mol of the diamine. It is however possible to use an excess of furfural up to, for example, 6 mols per mol of diamine. The reaction mixture should preferably contain at least 20% by weight of diethyl ether, based on the combined weight of furfural, diamine and ether, but there is no advantage in using more than 95% of the ether. It is desirable to use anhydrous reagents and exclude water from the reaction mixture as the presence of water causes an impure product to be obtained.

The duration of the reaction is of the order of a few minutes to a few hours, depending on the temperature chosen.

The product can be isolated from the reaction mixture by filtration, and purified by the usual methods, though only washing, e.g. with hexane, and drying is necessary to give a product melting at 90°–91°C.

Bis-(4-furfurylidenamino-phenyl)-methane can be used in photographic mixtures as described in Belgian Pat. No. 660,874. It can also advantageously be used for the production of cellular materials, by reaction with maleic anhydride.

The following Example illustrates the invention.

EXAMPLE 19.8 g. of the bis-(4-amino-phenyl)-methane are added, over the course of 5 minutes at ambient temperature, with stirring, to a solution of 19.8 g. of furfural in 100 cm³ of diethyl ether which has previously been dried over calcium chloride.

The whole is stirred for 4 hours at ambient temperature (25°C) and the precipitate which has formed is then filtered off, washed with hexane and kept for 15 hours under reduced pressure (5 mm Hg.) at 50°C. 22 g. of a powder, m.p. 90°–91°C., are finally obtained.

Percentage analysis, measurement of the molecular weight and investigation by infra-red spectrography show that it is bis-(4-furfurylidenamino-phenyl)-methane.

We claim:

1. Process for the preparation of solid bis-(4-furfurylidenamino-phenyl)-methane, which comprises contacting furfural and bis-(4-amino-phenyl)-methane in a diethyl ether medium.

2. Process according to claim 1, in which substantially two moles of furfural are used per mole of the said diamine.

3. Process according to claim 1 in which the reaction is carried out at 20°–25°C.

* * * * *